(12) United States Patent
Wang et al.

(10) Patent No.: US 11,814,827 B2
(45) Date of Patent: Nov. 14, 2023

(54) SHOWER APPARATUS

(71) Applicant: RUNNER(XIAMEN) CORP., Fujian (CN)

(72) Inventors: Yongsheng Wang, Fujian (CN); Dingjun Wang, Fujian (CN); Taoyan Zhang, Fujian (CN); Zhisheng Li, Fujian (CN); Wen Go, Fujian (CN); Lizhong Liao, Fujian (CN)

(73) Assignee: RUNNER(XIAMEN) CORP.

( * ) Notice: Subject to any disclaimer, the term of this patent is extended or adjusted under 35 U.S.C. 154(b) by 569 days.

(21) Appl. No.: 17/139,389

(22) Filed: Dec. 31, 2020

(65) Prior Publication Data

US 2021/0324615 A1    Oct. 21, 2021

(30) Foreign Application Priority Data

Apr. 16, 2020   (CN) .......................... 202010300182.X

(51) Int. Cl.
*E03C 1/04*  (2006.01)
*E03C 1/042*  (2006.01)
*A61M 39/22*  (2006.01)

(52) U.S. Cl.
CPC .............. *E03C 1/0408* (2013.01); *E03C 1/04* (2013.01); *E03C 1/042* (2013.01); *A61M 39/223* (2013.01); *E03C 2201/30* (2013.01)

(58) Field of Classification Search
CPC .......... E03C 1/0408; E03C 1/04; E03C 1/042; E03C 2201/30; E03C 1/0403; E03C 1/023; A61M 39/223; F16K 11/00; F16K 11/074; F16K 27/003
See application file for complete search history.

(56) References Cited

U.S. PATENT DOCUMENTS

| | | | |
|---|---|---|---|
| 6,832,396 B1 * | 12/2004 | Lin ........................ | E03C 1/042 4/677 |
| 2016/0341325 A1 * | 11/2016 | Ye ......................... | F16K 19/006 |
| 2020/0208384 A1 * | 7/2020 | Wang .................... | E03C 1/0408 |

* cited by examiner

*Primary Examiner* — Christine J Skubinna
(74) *Attorney, Agent, or Firm* — Jose Cherson Weissbrot

(57) ABSTRACT

The present invention discloses a shower apparatus, which comprises an upper body, a lower body and a mixing valve, the upper body and lower body are interconnected and fixed, the upper body is provided with a capacious space, the mixing valve is placed within the capacious space; the lower body comprises a cold water inlet channel, a hot water inlet channel and a mixing water outlet, the upper body comprises a cold water crossing channel, a hot water crossing channel and a mixing water crossing channel, the upper body comprises a cold water crossing channel, a hot water crossing channel and a mixing water crossing channel, the cold inlet channel, the hot inlet channel and the mixed water outlet are hermetically connected to the cold water crossing channel, the hot water crossing channel and the mixed water crossing channel, respectively. The shower apparatus adopts modular split design, which takes the lower body as the base platform, so that the upper body can be replaced with different functions, with simple structure and low cost, and satisfy the matching of platform functions at the same time; in addition, the shower apparatus integrates the automatic stop valve group into the upper body to realize modular assembly, with simple structure and convenient structure.

10 Claims, 11 Drawing Sheets

Fig.1 (Abstract Fig)

SHOWER APPARATUS

FIELD AND BACKGROUND OF THE INVENTION

1. Technical Field

The present invention relates to a shower apparatus.

2. Description of Related Art

Most of the existing in-wall shower valves on the market are one-piece copper body molding, which are complicated and costly to process, and cannot be platform unfolded; therefore, it is necessary to develop a new shower valve that can meet the same function, reduce cost, and match different shower functions.

BRIEF SUMMARY OF THE INVENTION

To overcome the defects mentioned above, the present invention provides a shower apparatus.

The present invention is realized by the following technical solution: a shower apparatus, which comprises an upper body, a lower body and a mixing valve, the upper body and lower body are interconnected and fixed, the upper body is provided with a capacious space, the mixing valve is placed within the capacious space; the lower body comprises a cold water inlet channel, a hot water inlet channel and a mixing water outlet, the upper body comprises a cold water crossing channel, a hot water crossing channel and a mixing water crossing channel, the upper body comprises a cold water crossing channel, a hot water crossing channel and a mixing water crossing channel, the cold inlet channel, the hot inlet channel and the mixed water outlet are hermetically connected to the cold water crossing channel, the hot water crossing channel and the mixed water crossing channel, respectively.

Preferably, the inlet of the cold water crossing channel, the inlet of the hot water crossing channel and the outlet of the mixed water crossing channel are all crossing convex portions and are equipped with a seal around the periphery; the outlet of the cold water inlet channel, the outlet of the hot water inlet channel and the outlet of the mixed water crossing channel are outlet concave portions.

Preferably, the mixing water outlet is also provided with a partition.

Preferably, the cold water crossing channel and hot water crossing channel are respectively provided with a cavity, the cavity is provided with a stop valve group.

Preferably, the water stop valve group works in conjunction with the outlet of the cold inlet channel or the hot inlet channel, the water stop valve group is symmetrically distributed on opposite sides of the capacious space.

Preferably, the water stop valve group comprises a bolt, a reset spring, a movable actuator and a gasket, the movable actuator is set in the bolt, the reset spring is between the bolt and the movable actuator, the gasket is attached to the bottom of the movable actuator.

Preferably, the mixing valve is a thermostatic valve group; the thermostatic valve group comprises a switch bolt group, a temperature control ring, a valve spool body and a temperature sensitive spool, the temperature sensitive spool is fixedly connected to the temperature control ring, the switch bolt group and the temperature control ring are integrated in the valve spool body and both are distributed on the same axis.

Preferably, the thermostatic valve group is attached at the bottom to an adapter seat body, the adapter seat body has a pressure balancing module embedded in it.

Preferably, the pressure balancing module comprises a body section, a balancing shaft and a piston, the body section is set in the adapter seat body, the balancing shaft is set in the body section, the piston is set in the balancing shaft.

Preferably, the upper body and lower body are interconnected and fixed using screws.

Compared to the prior art, the present invention has the following beneficial effects: the shower apparatus adopts modular split design, which splits the valve body into an upper body and a lower body, takes the lower body as the base platform, so that the upper body can be replaced with different functions, with simple structure and low cost, and satisfy the matching of platform functions at the same time; in addition, the shower apparatus integrates the automatic stop valve group into the upper body to realize modular assembly, with simple structure and convenient structure.

BRIEF DESCRIPTION OF THE DRAWINGS

In order to more clearly illustrate the technical scheme of the invention, a brief description of the drawings required to be used in embodiments or prior art descriptions will be given below, and it will be apparent that the drawings in the following description are only some examples of the invention, and that other drawings may be obtained from these drawings without creative labor on the part of one of ordinary skill in the art.

DESCRIPTION OF THE PREFERRED EMBODIMENTS

Figure 1:
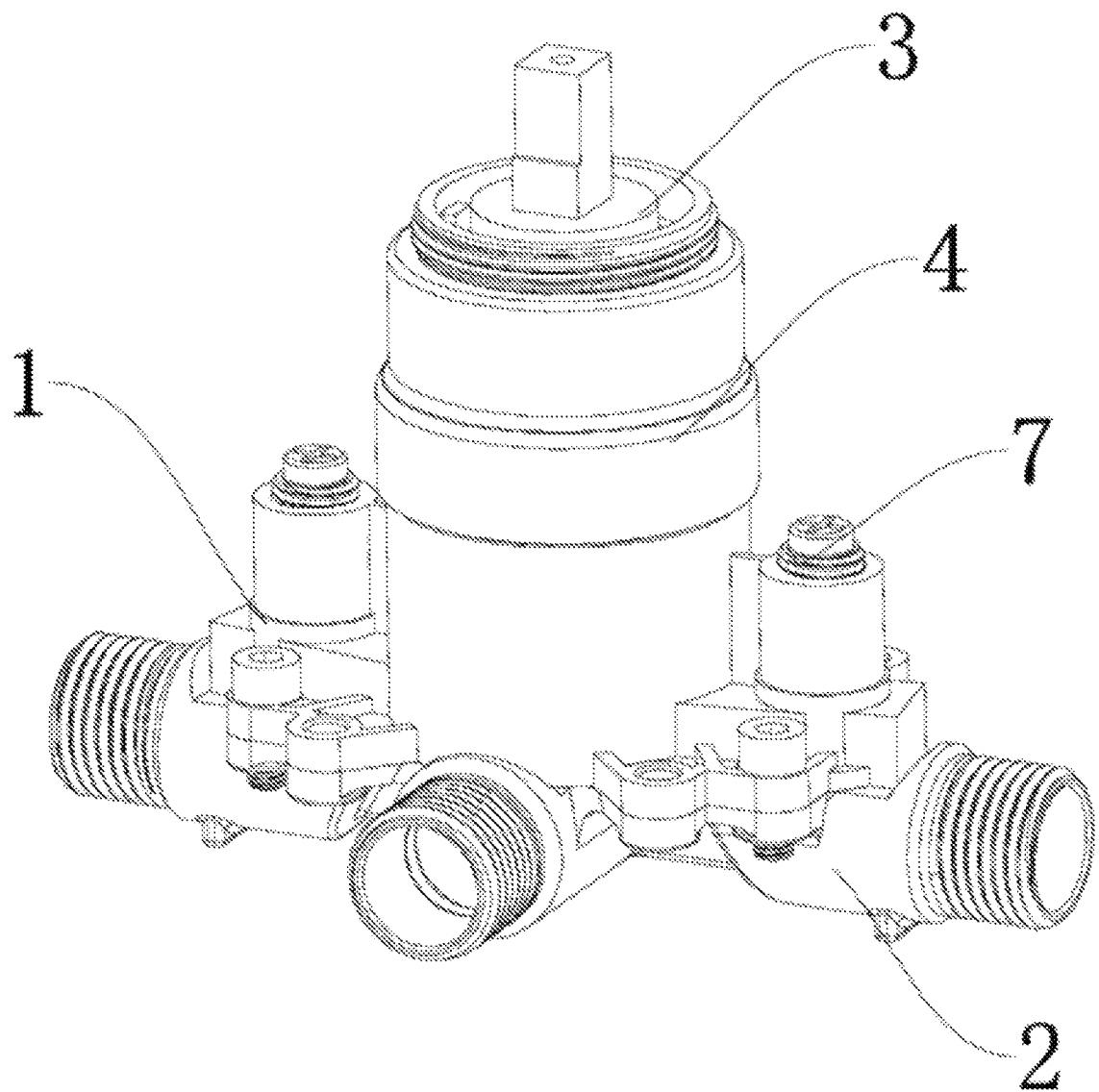
FIG. 1 is a three-dimensional view of the first embodiment of the present invention.
Figure 2:
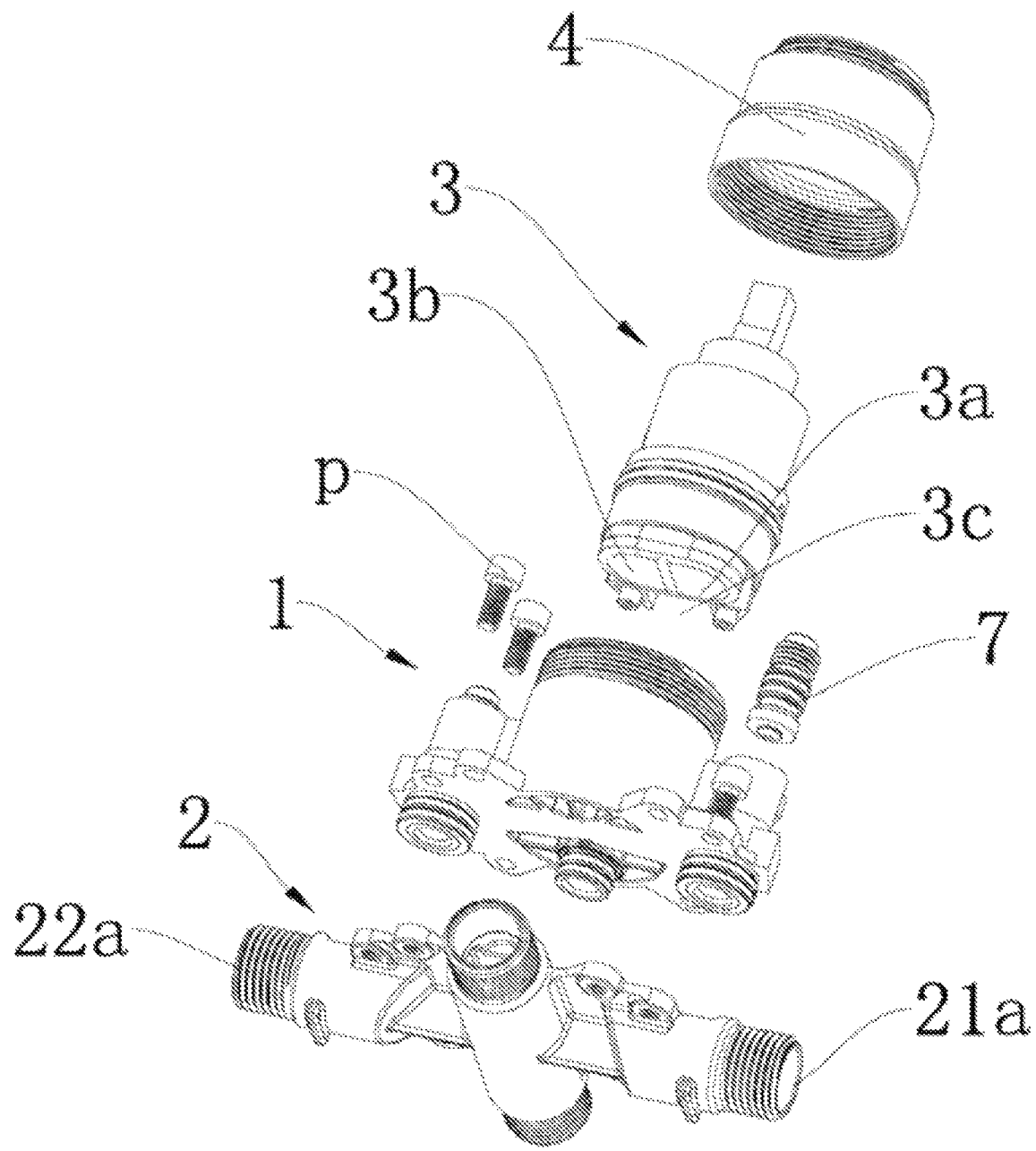
FIG. 2 is a decomposed diagram of the first embodiment of the present invention.
Figure 3:
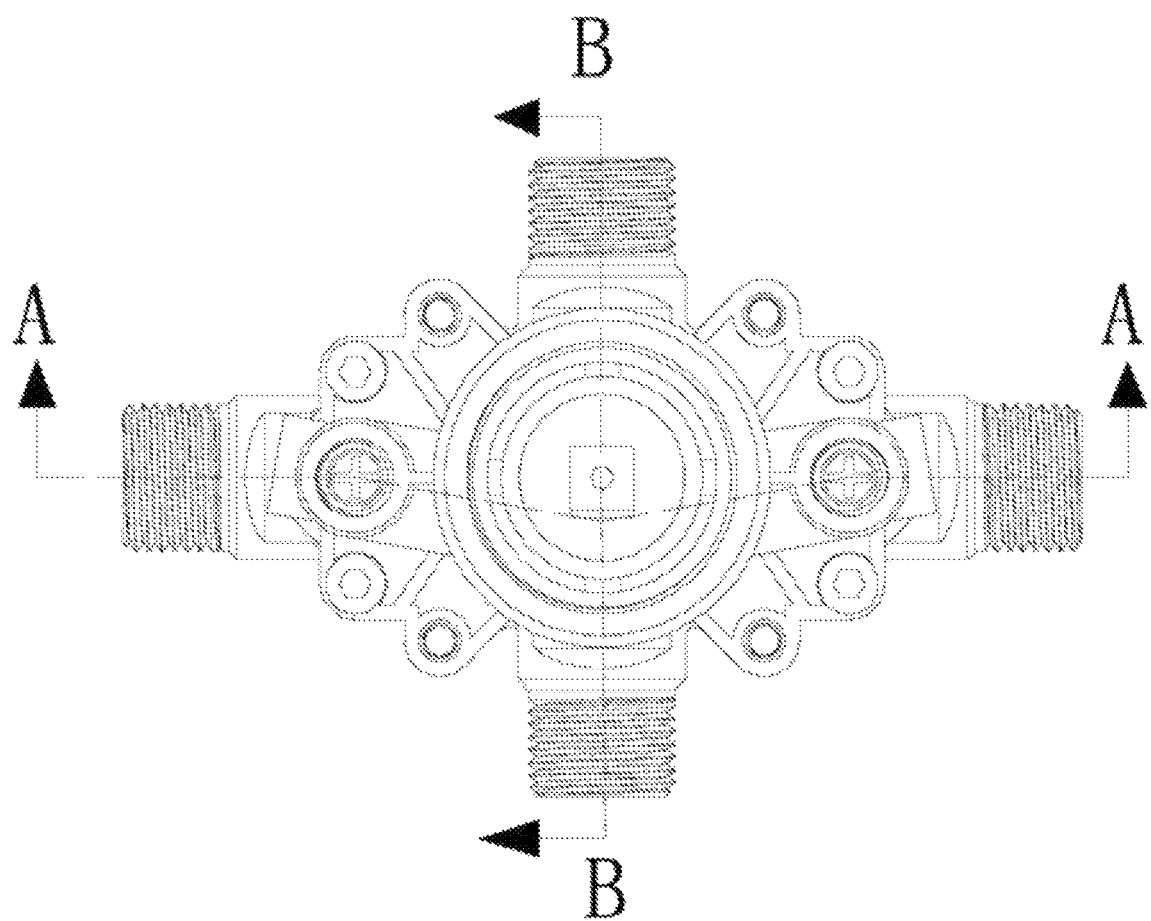
FIG. 3 is a top view of the first embodiment of the present invention.
Figure 4:
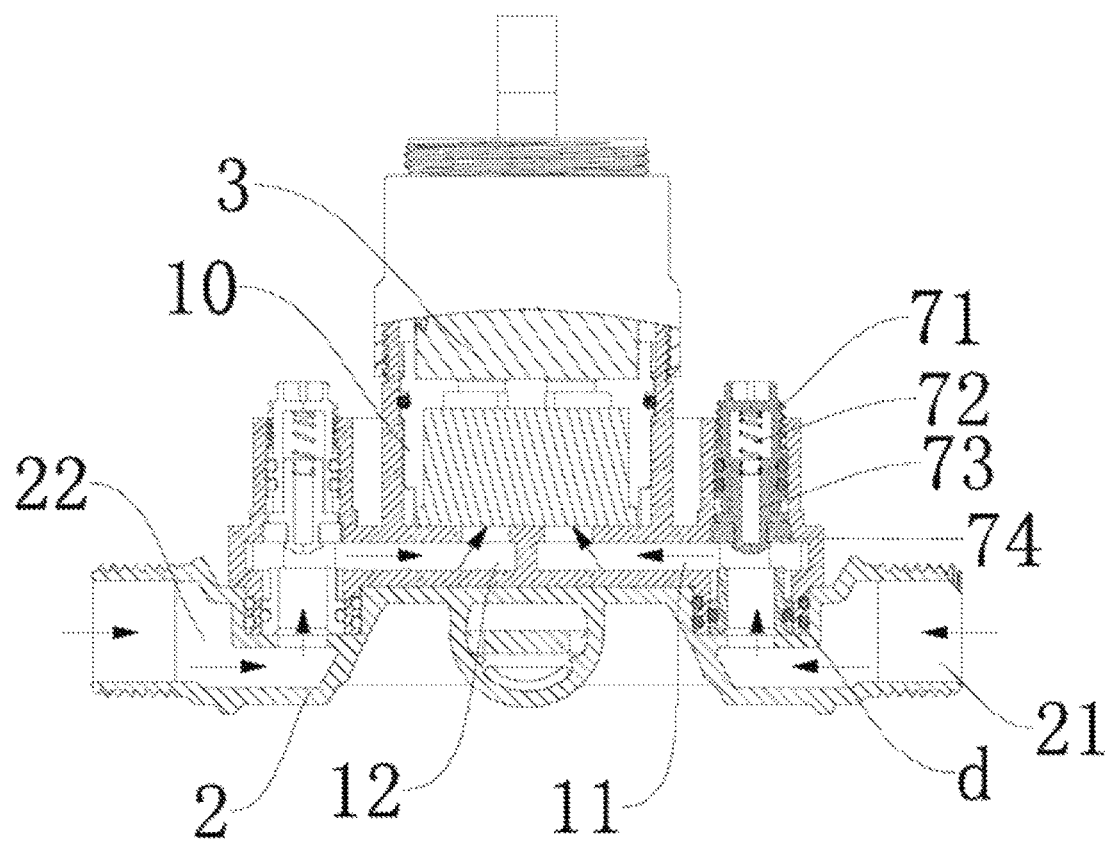
FIG. 4 is a sectional view at A-A in FIG. 3.
Figure 5:
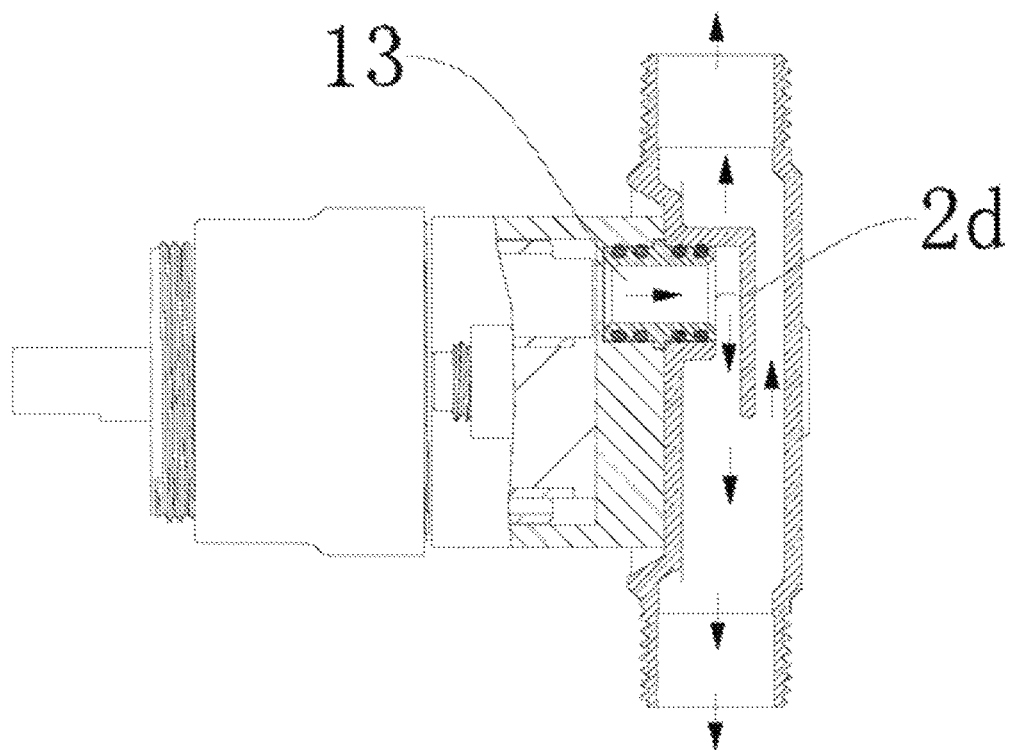
FIG. 5 is a sectional view at B-B in FIG. 3.
Figure 6:
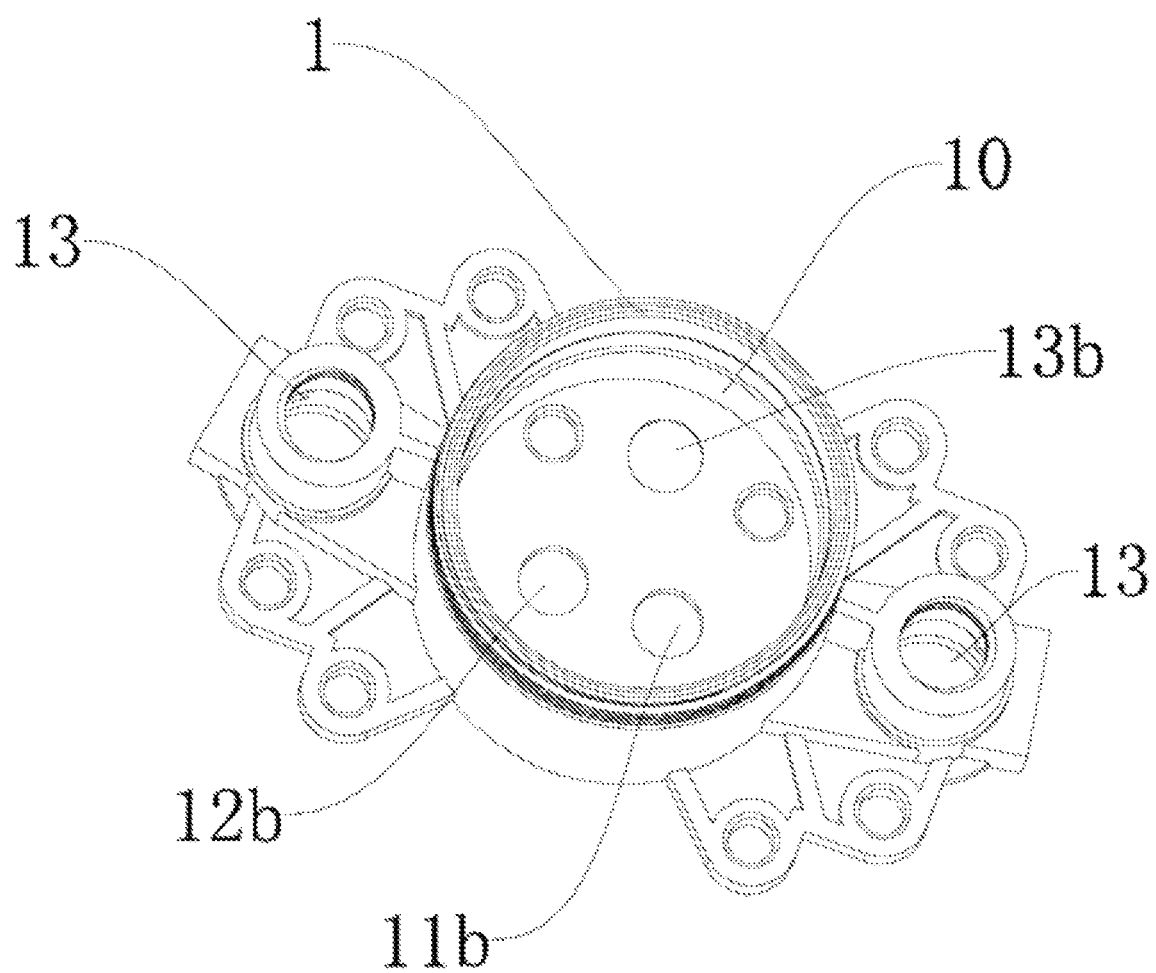
FIG. 6 is a three-dimensional view of the upper body of the present invention.
Figure 7:
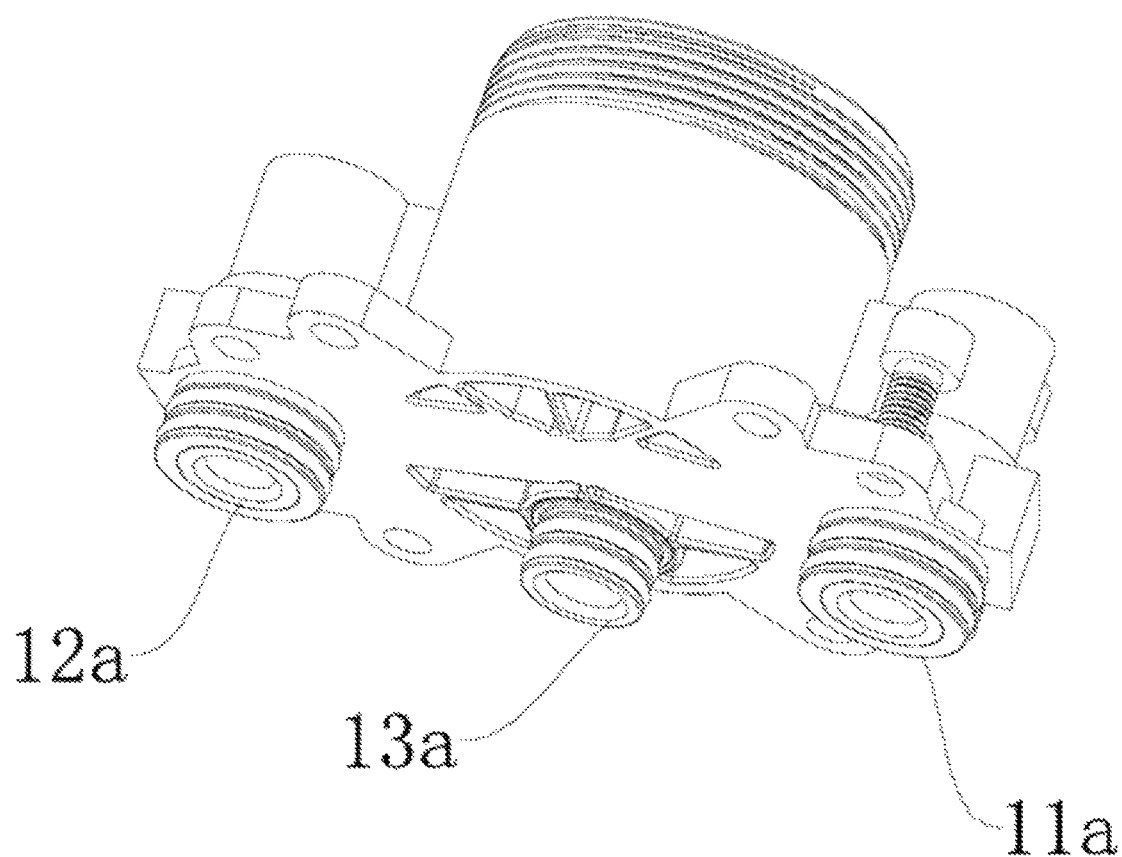
FIG. 7 is a stereoscopic view of the upper body of the present invention.
Figure 8:
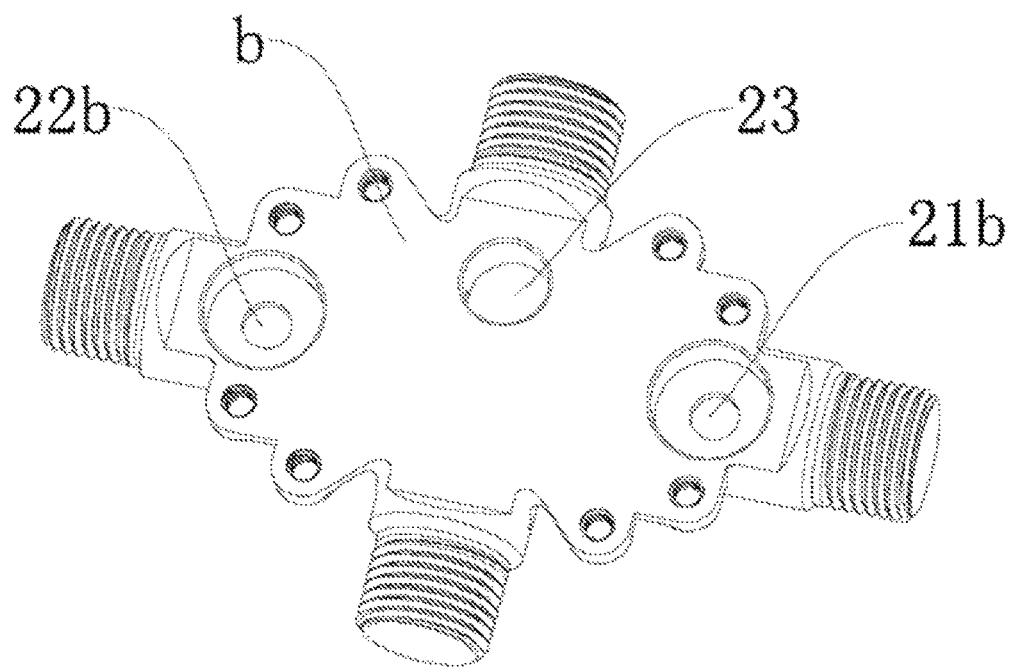
FIG. 8 is a stereoscopic view of the lower body of the present invention.
Figure 9:
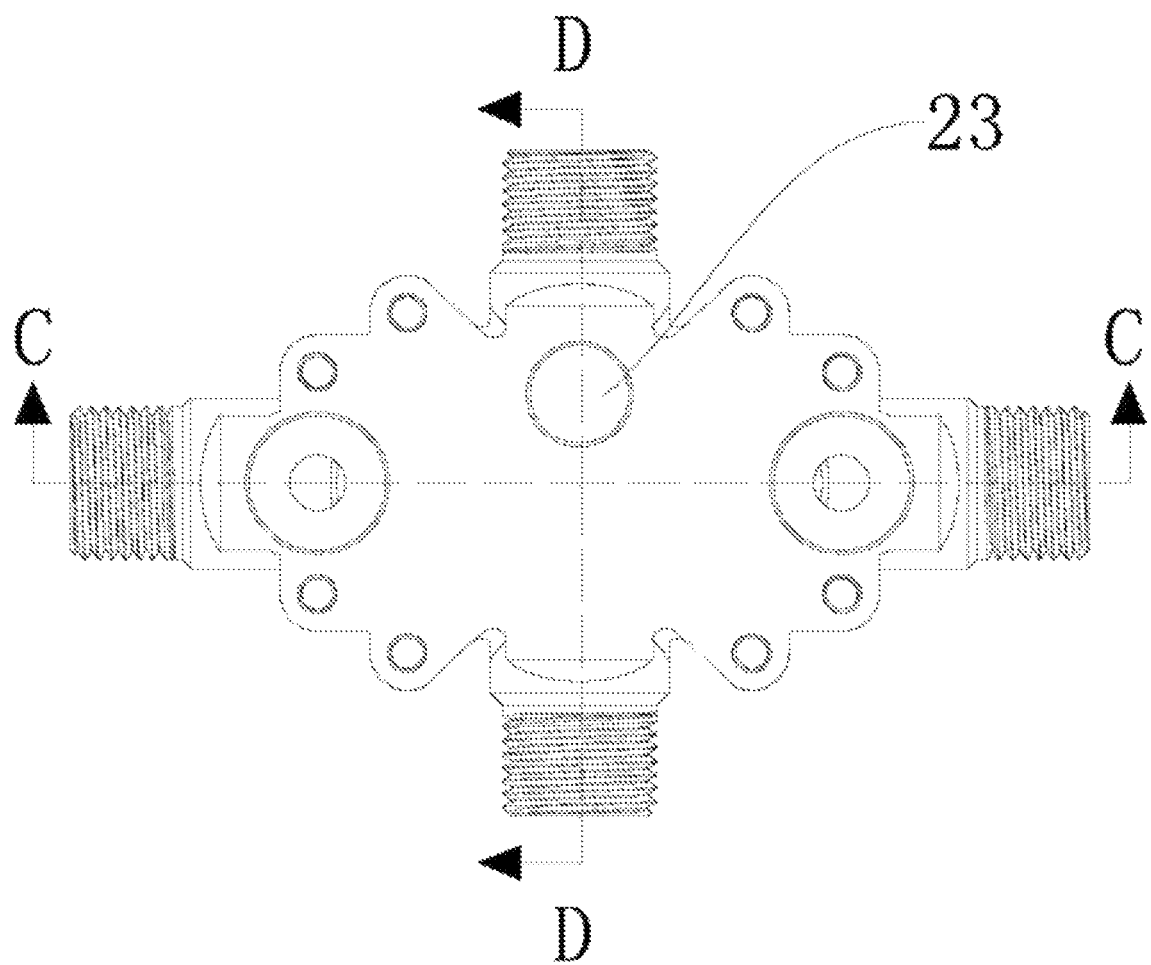
FIG. 9 is a top view of the lower body of the present invention.
Figure 10:
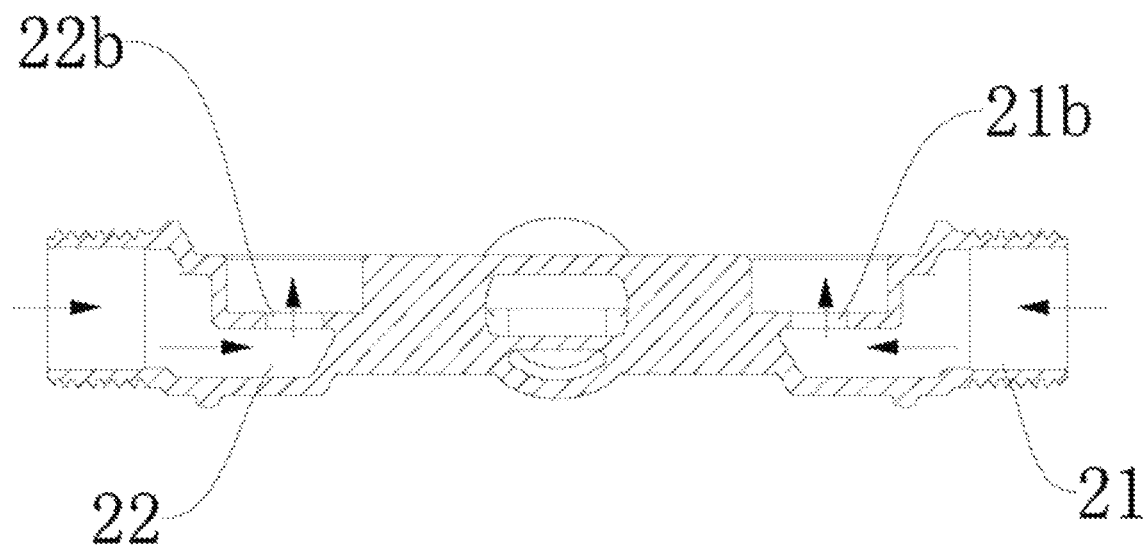
FIG. 10 is a sectional view at C-C in FIG. 9.
Figure 11:
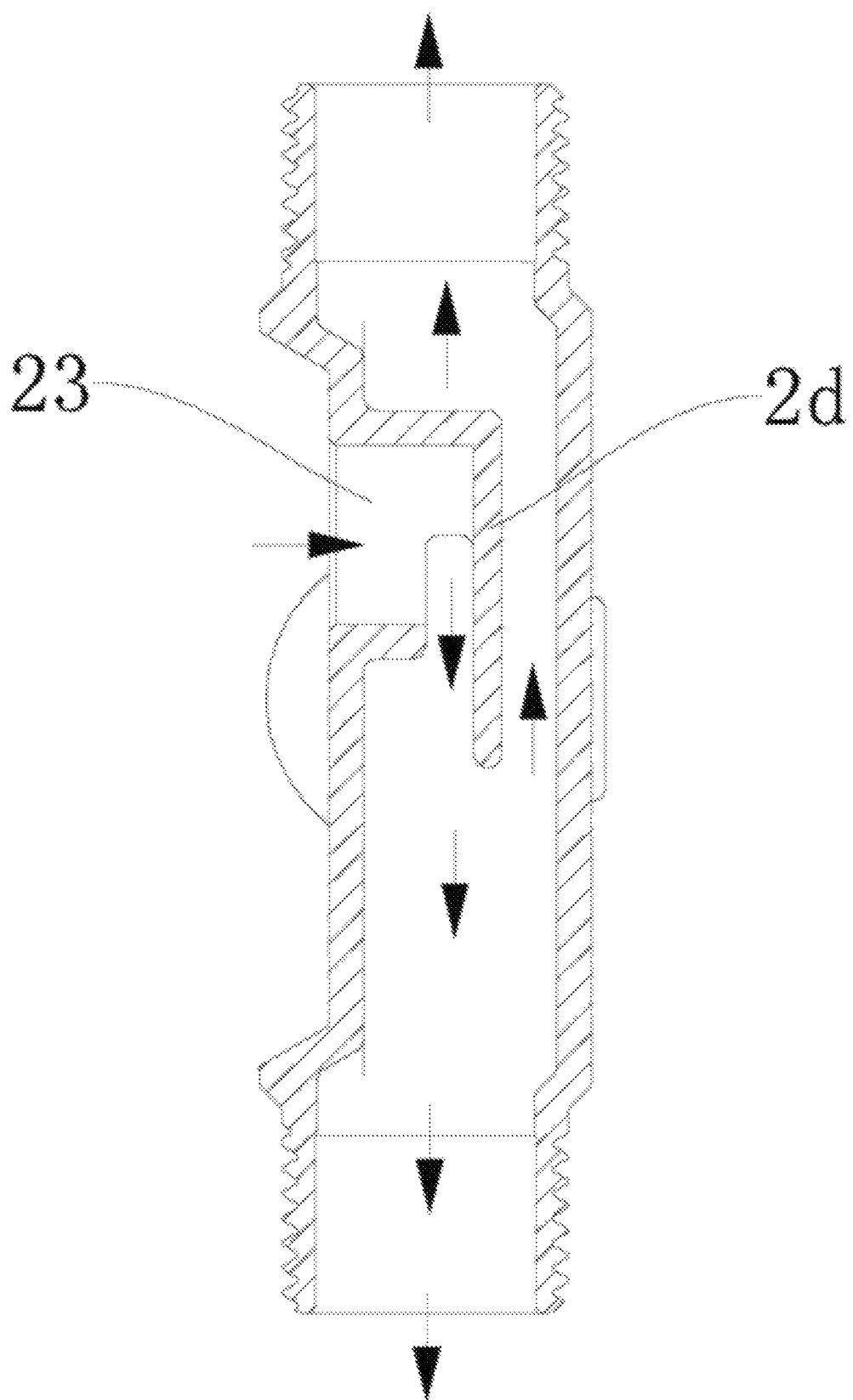
FIG. 11 is a sectional view at D-D in FIG. 9.
Figure 12:
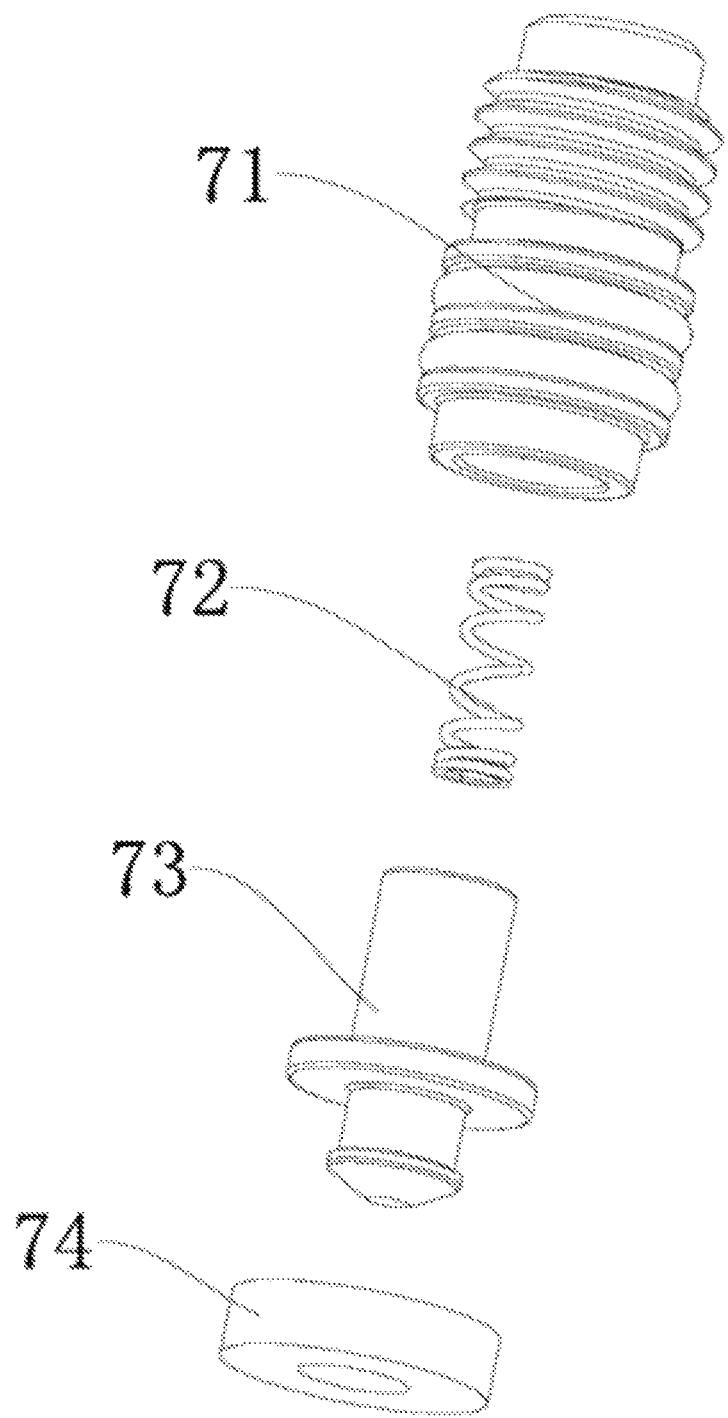
FIG. 12 is a decomposed view of the stop valve group of the present invention.

The following will be a clear and complete description of the technical scheme of the embodiments of the invention in conjunction with the drawings in the embodiments, and it is clear that the embodiments described are only some, but not all, of the embodiments of the invention. Based on the embodiments of the present invention, all other embodiments obtained by one of ordinary skill in the art without performing inventive work are within the scope of protection of the present invention.

Reference is made to FIGS. 1 to 12 of the specification, which are the first embodiment of the present invention. A shower apparatus comprises an upper body 1, a lower body 2 and a mixing valve 3, the upper body 1 and the lower body 2 is connected to each other, the mixing valve 3 is mounted in the upper body 1; wherein the lower body 2 comprises a cold inlet channel 21 and a hot inlet channel 22, the inlets 21a and 22a of the cold inlet channel and the hot inlet channel are located on the sides of the lower body 2, and the outlets of the cold inlet channel and the hot inlet channel 21b and 22b are located on an upper surface b of the lower body 2, which fits correspondingly with the bottom of the upper body 1, and the inlet and outlet of the water inlet channel are not set in the same plane, wherein a mixing water outlet 23 is also opened on the upper surface b. Preferably, the mixing water outlet 23 is also provided with a partition 2d, which is capable of directing the mixed water flow when it rushes against the partition 2d, the water flow thus acts as a buffer.

the lower body 2 and upper body 1 are tightly connected using screws p, wherein the upper body 1 includes a capacitive space 10, and the above-mentioned mixing valve 3 is set in the capacitive space 10 and fixed using the spool gland 4; the upper body 1 is opened with a cold water crossing channel 11, a hot water crossing channel 12 and a mixing water crossing channel 13, wherein the inlet 11a of the cold water crossing channel is connected to the cold inlet channel 21 and the inlet 12a of the hot water crossing channel is connected to the hot inlet channel 22, in addition, the outlet 11b of the cold water crossing channel, the outlet 12b of the hot water crossing channel and the outlet 13b of the mixed water crossing channel are all located in the capacious space 10 and are connected to the cold water channel 3a, the hot water channel 3b and the mixed water channel 3c of the mixing valve 3.

The cold water channel 11, the hot water channel 12 and the mixed water channel 13 are hermetically connected to the cold inlet channel 21, the hot inlet channel 22 and the mixed water outlet 23 respectively, preferably, the inlet 11a of the cold water channel, the inlet 12a of the hot water channel and the outlet 13a of the mixed water channel of the upper body are all crossing convex portions and there is a seal ring d around the outer circumference, and the outlet 21b of the cold water inlet channel, the outlet 22b of the hot water inlet channel and the mixed water outlet 23 of the lower body are outlet recesses, and the crossing convex portions are correspondingly set in the above-mentioned outlet recesses, which then enables each crossing outlet and outlet to seal and cooperate with each other to pass water.

Further, the upper body has a cavity 13 on the cold water crossing channel 11 and the hot water crossing channel 12, and the cavity 13 is provided with a water stop valve group 7, and the water stop valve group 7 cooperates with the cold water inlet channel and the hot water inlet channel outlet 21b and 22b of the lower body, and the water stop valve group 7 is symmetrically distributed on the opposite sides of the capacity space 10 of the upper body, that is, located on the side of the capacity space; the stop valve group 7 is a unidirectional stop valve group and is installed in the upper body 1, wherein the stop valve group 7 comprises a bolt 71, a return spring 72, a movable actuator 73 and a gasket 74, the movable actuator 73 is partially inserted into the bolt 71, the return spring 72 is located between the bolt 71 and the movable actuator 73, the gasket 74 is attached to the bottom of the movable actuator 73. When the incoming water pressure is offset against the gasket 74, the reset spring 72 is compressed, the movable actuator 73 drives the gasket 74 to move, and the water flows into the cold inlet 21 or the hot inlet 22 through the flow channel; when the water pressure disappears, the reset spring 72 is reset, and the movable actuator 73 links the gasket 74 to move, block the incoming water of the cold inlet 21 or hot inlet 22, so as to ensure that the water flows do not flow into each other. In the preferred embodiment, the lower body 2 described above is made of copper, and the upper body 1 and the stop valve group 7 are made of plastic, thus utilizing a partly plastic material instead of a partly metal housing, and reducing costs.

When the user turns on the water flow, cold water flows sequentially from the cold inlet channel 21 of the lower body and the cold water crossing channel 11 of the upper body into the cold water channel 3a of the mixing valve, and at the same time, hot water flows sequentially from the hot inlet channel 22 of the lower body and the hot water crossing channel 12 of the upper body into the hot water channel 3b of the mixing valve, after which the cold water and the hot water mix in the mixing valve 3 and pass through its mixing water channel 3c exits and flows from the mixing water crossing channel 13 to the mixing water outlet 23 of the lower body and ultimately out of the mixing water outlet pipe for human use. The modular design of the shower apparatus splits the valve body into an upper and lower body, with the lower body serving as the base platform on which the upper body can be replaced for different functions, which is simple and low cost and allows for the matching of platform functions; furthermore, the automatic water stop valve group is embedded into the upper body of the shower apparatus to realize modular assembly, with simple structure and convenience.

Figure 13:
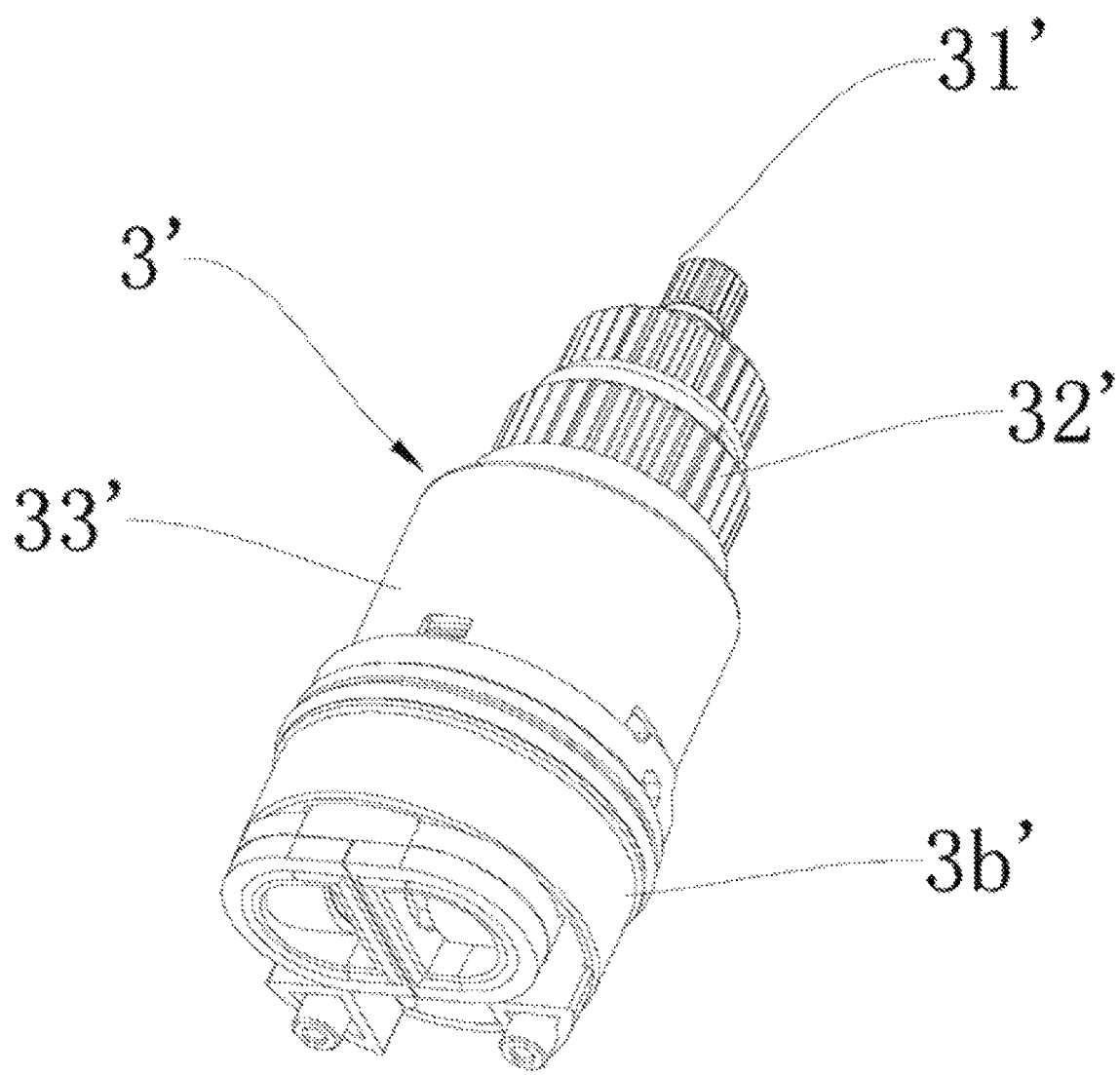
FIG. 13 is a three-dimensional view of the thermostatic valve group in the second embodiment of the present invention.
Figure 14:
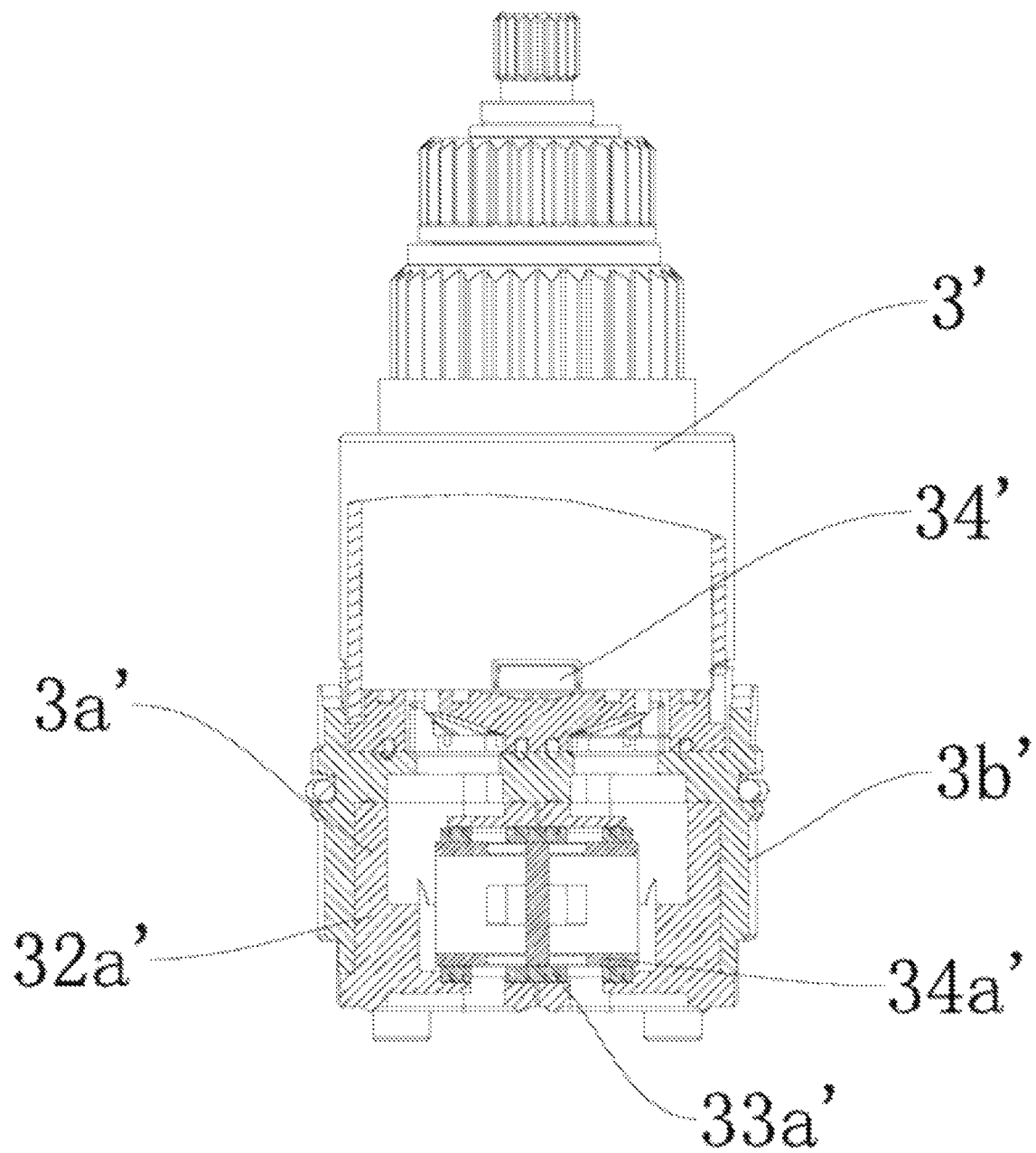
FIG. 14 is a partial sectional view of the thermostatic valve group in the second embodiment of the present invention.

Referring to FIGS. 13 and 14, which is the second embodiment of the present invention, only the differences from the first embodiment are described in detail herein, and the same will not be repeated. A shower apparatus comprises an upper body 1, a lower body 2 and a thermostatic valve group 3', the thermostatic valve group 3' comprises a switch bolt group 31', a temperature control ring 32', a valve spool body 33' and a temperature sensitive spindle 34, the temperature of the mixed hot and cold water is controlled by the temperature sensing mandrel 34', which is fixedly connected with the temperature control ring 32', and the temperature sensing mandrel 34' automatically compensates for the cold and hot water inlet ratio by sensing the change of the cold and hot water inlet temperature to ensure the constant temperature of the outlet water; in addition, the opening and closing of the water mixture at a defined temperature, which is regulated by the thermostat ring 32', is controlled by the rotation of the switching plug group 31', which can, for example, achieve the opening and closing of the water circuit by the coordination of the moving and static pieces. Preferably, the thermostatic valve set 3' is also connected to the bottom of the thermostatic valve set 3' with a pressure balancing module 3a' which is connected to the bottom of the thermostatic valve set 3' using an adapter seat body 3b', wherein the pressure balancing module 3a' includes a body portion 32a', a balance shaft 33a' and a piston 34a', which body portion 32a' is set within the adapter body 3b', the balance shaft 33a' is disposed transversely in this main body 32a', and the piston 34a' is set in this balance shaft 33a', so that, due to the pressure balancing module set in the body of the adapter, when the cold and hot water inlet pressures are different, the piston 34a' moves axially in the balance axis 33a' and automatically compensates the cold and hot water inlet ratios to reach a balanced state, so as to ensure that the temperature of water outlet will not be hot and cold with pressure change. The shower device integrates the switch and temperature control in the same axis, forming coaxial dual control function, which can both switch on and off the water and adjust the temperature, integrating the dual function of boiling and adjusting the temperature, making the operation simpler, and capable of constant temperature and anti-scald, very safe and reliable.

The foregoing expressly states and describes preferred embodiments of the invention and, as previously stated, it is to be understood that the invention is not limited to the form disclosed herein and is not to be regarded as exclusive of other embodiments, but may be used in a variety of other combinations, modifications and circumstances and is capable of being altered within the scope of the invention idea described herein by the above teachings or by skill or knowledge in the related field. And the alterations and changes made by persons in the art which do not depart from the spirit and scope of the invention shall be within the protection of the claims appended hereto.

What is claimed is:

1. A shower apparatus, characterized in that it comprises an upper body, a lower body and a mixing valve, the upper body and lower body are interconnected and fixed, the upper body is provided with a capacious space, the mixing valve is placed within the capacious space; the lower body comprises a cold water inlet channel, a hot water inlet channel and a mixing water outlet, the upper body comprises a cold water crossing channel, a hot water crossing channel and a mixing water crossing channel, the upper body comprises a cold water crossing channel, a hot water crossing channel and a mixing water crossing channel, the cold inlet channel, the hot inlet channel and the mixed water outlet are hermetically connected to the cold water crossing channel, the hot water crossing channel and the mixed water crossing channel, respectively.

2. A shower apparatus according to claim 1, characterized in that the inlet of the cold water crossing channel, the inlet of the hot water crossing channel and the outlet of the mixed water crossing channel are all crossing convex portions and are equipped with a seal around the periphery; the outlet of the cold water inlet channel, the outlet of the hot water inlet channel and the outlet of the mixed water crossing channel are outlet concave portions.

3. A shower apparatus according to claim 1, characterized in that the mixing water outlet is also provided with a partition.

4. A shower apparatus according to claim 1, characterized in that the cold water crossing channel and hot water crossing channel are respectively provided with a cavity, the cavity is provided with a stop valve group.

5. A shower apparatus according to claim 4, characterized in that the water stop valve group works in conjunction with the outlet of the cold inlet channel or the hot inlet channel, the water stop valve group is symmetrically distributed on opposite sides of the capacious space.

6. A shower apparatus according to claim 4, characterized in that the water stop valve group comprises a bolt, a reset spring, a movable actuator and a gasket, the movable actuator is set in the bolt, the reset spring is between the bolt and the movable actuator, the gasket is attached to the bottom of the movable actuator.

7. A shower apparatus according to claim 1, characterized in that the mixing valve is a thermostatic valve group; the thermostatic valve group comprises a switch bolt group, a temperature control ring, a valve spool body and a temperature sensitive spool, the temperature sensitive spool is fixedly connected to the temperature control ring, the switch bolt group and the temperature control ring are integrated in the valve spool body and both are distributed on the same axis.

8. A shower apparatus according to claim 7, characterized in that the thermostatic valve group is attached at the bottom to an adapter seat body, the adapter seat body has a pressure balancing module embedded in it.

9. A shower apparatus according to claim 8, characterized in that the pressure balancing module comprises a body section, a balancing shaft and a piston, the body section is set in the adapter seat body, the balancing shaft is set in the body section, the piston is set in the balancing shaft.

10. A shower apparatus according to claim 8, characterized in that the upper body and lower body are interconnected and fixed using screws.

* * * * *